(12) United States Patent
Birkner

(10) Patent No.: US 8,053,213 B2
(45) Date of Patent: Nov. 8, 2011

(54) DETECTION OF PCR PRODUCTS IN GEL ELECTROPHORESIS

(75) Inventor: Christian Birkner, Uffing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/876,320

(22) Filed: Sep. 7, 2010

(65) Prior Publication Data

US 2010/0330579 A1  Dec. 30, 2010

Related U.S. Application Data

(63) Continuation of application No. PCT/EP2009/002264, filed on Mar. 27, 2009.

(30) Foreign Application Priority Data

Apr. 8, 2008 (EP) .................................... 08006994

(51) Int. Cl.
*C12P 19/34* (2006.01)
*C12Q 1/68* (2006.01)
*C07H 21/00* (2006.01)
*C07H 21/02* (2006.01)

(52) U.S. Cl. ......... 435/91.1; 435/6; 536/23.1; 536/24.3; 536/26.6

(58) Field of Classification Search ............. 435/6, 91.1; 536/23.1, 24.3, 26.6
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,965,188 A | 10/1990 | Mullis et al. |
| 5,310,652 A | 5/1994 | Gelfand et al. |
| 5,322,770 A | 6/1994 | Gelfand |
| 5,407,800 A | 4/1995 | Gelfand et al. |
| 5,658,751 A | 8/1997 | Yue et al. |
| 6,106,777 A | 8/2000 | Fujita et al. |
| 6,569,627 B2 | 5/2003 | Wittwer et al. |
| 6,814,934 B1 | 11/2004 | Higuchi |

FOREIGN PATENT DOCUMENTS

| | | |
|---|---|---|
| WO | 2006/121423 A3 | 11/2006 |
| WO | 2008/052742 A1 | 5/2008 |

OTHER PUBLICATIONS

International Search Report issued Jun. 17, 2009 in PCT Application No. PCT/EP2009/002264.
International Preliminary Report on Patentability issued Mar. 4, 2010 in PCT Application No. PCT/EP2009/002264.
Eldering, Joyce A. et al., Development of a PCR method for mycoplasma testing of Chinese hamster ovary cell cultures used in the manufacture of recombinant therapeutic proteins, Biologicals, 2004, pp. 183-193, vol. 32.
Garcia-Canas, Virginia et al., Ultrasensitive Detection of Genetically Modified Maize DNA by Capillary Gel Electrophoresis with Laser-Induced Fluorescence Using Different Fluorescent Intercalating Dyes, Journal of Agriculture and Food Chemistry, 2002, pp. 4497-4502, vol. 50.
Gudnason, Haukur et al., Comparison of multiple DNA dyes for real-time PCR: effects of dye concentration and sequence composition on DNA amplification and melting temperature, Nucleic Acids Research, Sep. 26, 2007, 8 pp., vol. 35, No. 19, e127.
Guttman, Andras, Chapter 13 Capillary Gel Electrophoresis, Methods in Molecular Biology, 1996, pp. 157-169, vol. 52.
Jin, X. et al., SYBR(R) Green 1 Nucleic Acid Gel Stain Provides a Sensitive Fluorescent Method for Detecting Gel Mobility Shift Products, FASEB J., 1996, Abstract #751, vol. 10, No. A1128.
Karlsen, Frank et al., SYBR Green I DNA staining increases the detection sensitivity of viruses by polymerase chain reaction, Journal of Virological Methods, 1995, pp. 153-156, vol. 55.
Larinov, Alexey et al., A standard curve based method for relative real time PCR data processing, BMC Bioinformatics, Mar. 21, 2005, p. 62, vol. 6, No. 1.
Roche, The LightCycler(R) 480 real-time PCR system: a verstatile platform for genetic variation research, Nature Methods, Mar. 3, 2008, pp. I-II, vol. 5, No. 3.
Sang, Fuming and Ren, Jicun, Capillary electrophoresis of double-stranded DNA fragments using a new fluorescence intercalating dye EvaGreen, J. Sep. Sci., 2006, pp. 1275-1280, vol. 29.
Schwartz, Herbert E. et al., Analysis of DNA restriction fragments and polymerase chain reaction products towards detection of the AIDS (HIV-1) virus in blood, Journal of Chromatography, 1991, pp. 267-283, vol. 559.

*Primary Examiner* — Jezia Riley

(57) ABSTRACT

Disclosed is a method for analyzing nucleic acids in a sample comprising the following steps: (i) adding a DNA binding dye containing a benzothiazolium or benzoxazolium group to the sample to be analyzed, (ii) carrying out a polymerase chain reaction, (iii) applying the sample to a gel matrix, (iv) separating the nucleic acid molecules according to their size by applying a voltage and (v) excitation with light of a suitable wavelength for the optical visualization of the nucleic acid/DNA binding dye complexes.

7 Claims, 5 Drawing Sheets c(RO27)= 0.8 µM c(SGI)= 0.8 µM c(RO27)= 0.8 µM c(SGI)= 0.8 µM c(RO27)= 4.0 µM c(SG1)= 4.0 µM c(RO27)= 4.0 µM c(SG1)= 4.0 µM

DETECTION OF PCR PRODUCTS IN GEL ELECTROPHORESIS

RELATED APPLICATIONS

This application is a continuation of PCT/EP2009/002264 filed Mar. 27, 2009 and claims priority to European application EP 08006994.1 filed Apr. 8, 2008.

FIELD OF THE INVENTION

The present invention concerns a simplified method in the field of nucleic acid analytics. The method according to the invention enables a gel electrophoretic nucleic acid determination to be carried out without gel staining because the dye is added to the sample containing nucleic acids.

BACKGROUND OF THE INVENTION

An electrophoretic separation of nucleic acids in gel matrices usually takes place either in agarose gels or in polyacrylamide gels. The resolving power is determined by the content of agarose in the gel in the case of agarose gels. In contrast, the resolving power of polyacrylamide gels is adjusted by the mixing ratio of acrylamide to bisacrylamide. The detection of nucleic acids in nucleic acid analytics with the aid of gel electrophoresis is based on the fact that fluorescent DNA binding dyes permanently bind non-covalently to nucleic acids and in their bound form enable nucleic acids to be located in the gel matrix after excitation with light of a suitable wavelength.

In classical gel electrophoresis the intercalating dye ethidium bromide was used for this purpose. However, due to the toxicity of ethidium bromide, alternative DNA binding dyes such as for example SYBR Green or SYBR Gold (Molecular Probes, Inc.) have been used for several years, the binding properties of which are not or not exclusively based on the principle of DNA intercalation.

In contrast to ethidium bromide, these dyes can also be used to detect PCR amplificates in real time PCR or qPCR since they do not substantially inhibit the PCR reaction (U.S. Pat. No. 6,569,627). There are other dyes apart from SYBR Green and SYBR Gold which can also be used in real time PCR (Gudnason, H., et al., Nucleic Acids Research 35(19) (2007) e127).

Furthermore, certain dyes exist for real time PCR applications which are especially suitable for thermal melting curve analyses such as the LIGHTCYCLER (Roche Diagnostics GmbH) 480 RO 27 dye (Roche Applied Science Cat. No.: 04 909 640 001). They are grouped together as HRM (high resolution melting) fluorescent dyes and are characterized in that they can be used in higher concentrations in the PCR without inhibiting the PCR reaction.

Capillary gel electrophoresis is also an important method for analyzing PCR products, for analyzing fragments from the restriction digestion, for mutation analytics and DNA sequencing due to its speed, the ability to automate and its high resolving power. LIF (laser induced fluorescence) detection plays an important role in this connection in order to make it possible to detect and quantify DNA in a highly sensitive manner and in a high dilution. In addition to the covalent coupling of fluorescent dyes to the DNA (by means of fluorescent labelled primers during DNA sequencing), the use of dsDNA intercalators plays a major role as a non-covalent method which enables DNA to be detected fluorimetrically and simply by means of stable dye-DNA complexes. The same intercalators are used for this as for the detection of DNA in gel electrophoresis (Sang, F., et al., J. Sep. Sci. 29 (2006)1275-1280).

The dyes used for electrophoresis are either admixed with the gel preparation before polymerization in the case of ethidium bromide, or the gel is stained after completion of the gel electrophoresis with the aid of an aqueous dye solution containing ethidium bromide or another dye. Furthermore, it has also been described that SYBR Green I can be added to the sample containing the nucleic acid before loading the gel, provided the nucleic acid is incubated with the dye for a further 15 minutes before being applied to the gel (Karlsen, F., et al., Journal of Virol. Methods 55 (1995) 153-156, and Jin, X., et al., FASEB J. 10 A1128 (1996) abstract # 751).

The staining methods for the gel electrophoretic analysis of nucleic acids known from the prior art thus have the disadvantage that the addition before polymerization only takes place with the mutagenic substance ethidium bromide, staining in a dye solution is time-consuming and laborious and requires large amounts of dye, or the addition of the dye immediately before loading the gel requires a longer incubation period.

SUMMARY OF THE INVENTION

The present invention therefore concerns a method for analyzing nucleic acids in a sample comprising the following steps
- adding a DNA binding dye containing a benzothiazole, a benzothiazolium or a benzoxazolium group to the sample to be analyzed
- carrying out a polymerase chain reaction
- applying the sample to a gel matrix
- separating the nucleic acid molecules according to their size by applying a voltage
- excitation with light of a suitable wavelength for the optical visualization of the nucleic acid/DNA binding dye complexes.

The method according to the present invention is particularly characterized in that the gel matrix is not pre-stained prior to the separation of the nucleic acid molecules and further in that the gel matrix is not stained after the separation of the nucleic acid molecules.

In a special embodiment the amplification is measured in real time during the PCR with the aid of the DNA binding dye.

The gel matrix preferably consists either of agarose or of polyacrylamide. If it is polyacrylamide, the gel matrix can also be in a capillary in order to carry out a capillary gel electrophoresis.

The DNA binding dyes are preferably selected from the groups consisting of RO 27, Syto 9, LC Green and LC Green+. RO 27 is particularly preferred in this case.

The DNA binding dyes are usually added to the sample at a concentration of 1-10 μM and preferably 2-4 μM.

Another aspect of the present invention concerns a kit, containing
- reagents for carrying out a polymerase chain reaction
- a vessel containing a DNA binding dye with a benzothiazole, benzothiazolium or benzoxazolium group and
- at least one gel matrix consisting of polyacrylamide.

The DNA binding dye is in turn preferably selected from a group consisting of RO 27, SYBR Green I, SYBR Green II, Syto 9, LC Green and LC Green+.

DETAILED DESCRIPTION OF THE INVENTION

Figure 1:
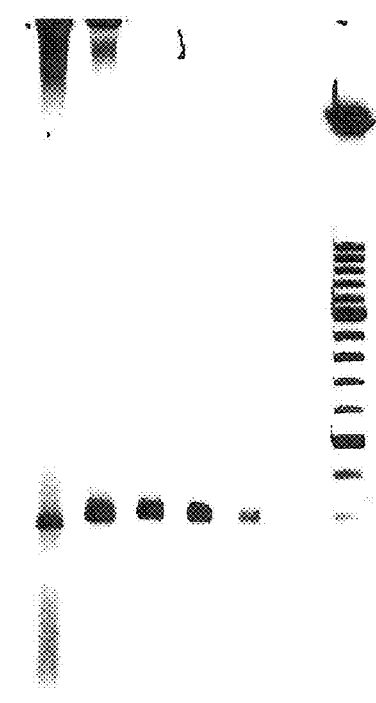
FIG. 1: Gel electrophoresis with subsequent detection of the amplificate by a LumiImager without (left) and with (right) restaining.
Figure 1:
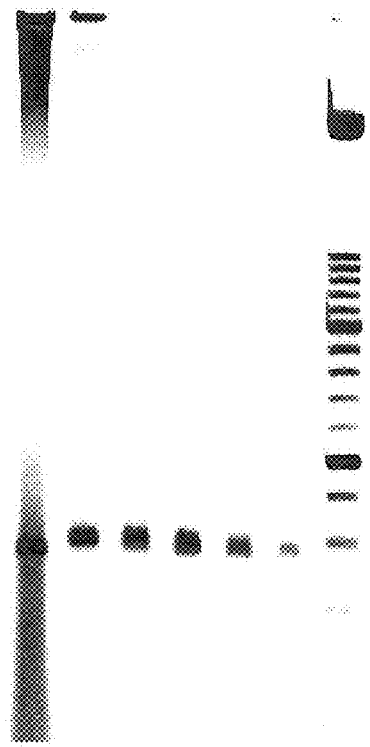

The origin of the present invention was the surprising finding that it is possible to add a real time PCR mixture containing a DNA binding dye directly to the PCR and namely at a concentration which is sufficient to allow omission of a subsequent staining of the PCR products, for example, with ethidium bromide or with SYBR Green I or SYBR Green II after the gel electrophoresis. These DNA binding dyes only emit a corresponding fluorescence signal after excitation with light of a suitable wavelength when they have bound to double-stranded nucleic acid. The detectability requires a strong, non-covalent binding of the fluorescent dye to the DNA.

Due to their cationic properties DNA binding dyes migrate in an unbound form towards the cathode during gel electrophoresis. The charge of the nucleic acids is, however, not sufficient for the nucleic acid/binding dye complex to migrate towards the anode during a gel electrophoresis.

Hence, the present invention concerns a method for analyzing nucleic acids in a sample comprising the following steps
adding a DNA binding dye containing a benzothiazolium or benzoxazolium group to the sample to be analyzed
carrying out a polymerase chain reaction (PCR)
applying the sample to a gel matrix
separating the nucleic acid molecules according to their size by applying a voltage
excitation with light of a suitable wavelength for the optical visualization of the nucleic acid/DNA binding dye complexes.

The method according to the present invention is particularity characterized in that the gel matrix is not pre-stained prior to the separation of the nucleic acid molecules and further in that the gel matrix is not stained after the separation of the nucleic acid molecules.

The sample to be analyzed is usually a mixture of nucleic acids which have been obtained from biological material such as for example cellular lysates. These lysates can be prepared by any standard methods. As a rule the nucleic acids present in the lysates are at least partially purified by methods known from the prior art before a PCR can be carried out by standard methods (U.S. Pat. No. 4,683,202, U.S. Pat. No. 4,683,195, U.S. Pat. No. 4,965,188). The nucleic acids present in the sample can either be DNA or RNA. In the case of RNA, the PCR is carried out in the form of a one-step RT-PCR in which the RNA is firstly reversely transcribed into a single-stranded cDNA with the aid of suitable enzymes and subsequently this cDNA is amplified to form a double-stranded end product (U.S. Pat. No. 5,407,800, U.S. Pat. No. 5,322,770, U.S. Pat. No. 5,310,652).

In a special embodiment the progress of the PCR reaction can be measured in real time during the amplification with the aid of the DNA binding dye (U.S. Pat. No. 6,569,627). This requires thermocyclers with optical modules which excite the DNA binding dye contained in the PCR reaction vessel during the PCR reaction and can subsequently detect the fluorescence signal emitted by this dye (e.g., U.S. Pat. No. 6,814,934, U.S. Pat. No. 6,106,777).

The DNA binding dyes are usually added to the sample at a concentration of 1-10 μM and preferably 2-4 μM. These concentrations do not usually lead to a measurable or significant inhibition of the polymerase catalysed PCR reaction in the case of the dyes that are to be used according to the invention.

The DNA binding dyes that are used according to the invention are those dyes whose binding to nucleic acids is not exclusively based on the principle of interacalation. This applies in particular to all fluorescent dyes containing a benzothiazole, benzothiazolium or benzoxazolium group. Benzothiazolium has the chemical structure:

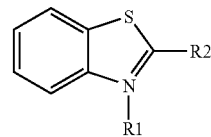

Benzoxazolium has an identical chemical structure except that the sulfur atom is replaced by an oxygen atom in the pentacyclic ring. These are preferably fluorescent dyes in which the benzothiazolium or benzoxazolium group is conjugated to the residue of the dye molecule via its 2' position (=R2). In contrast R1 is any substituent and is preferably an optionally substituted $C_1$-$C_6$ alkyl.

In a first embodiment they are in particular molecules having the following consensus structure:

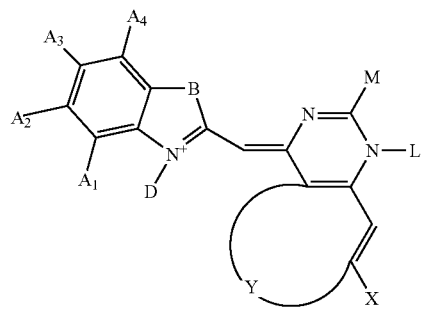

in which

A1, A2, A3 and A4 are hydrogen or a representative of A1, A2, A3 is a halogen,

B is either sulfur or oxygen,

D is either an unsubstituted or a substituted $C_1$-$C_6$ alkyl.

X is either hydrogen or a methoxy group,

Y is selected from a group consisting of S, O, N—R where R=$C_1$-$C_6$ alkyl, and Z1-C=C—Z2, where Z1 and Z2 independently of one another either denote hydrogen or a methoxy group.

L is either $CH_3$ or phenyl,

M is either phenyl or a substituted or unsubstituted $C_1$-$C_{18}$ amino-alkyl.

Examples of this are:

RO 03:

RO 04:

RO 11:

RO 12:

RO 13:

RO 14:

RO 26:

RO 28:

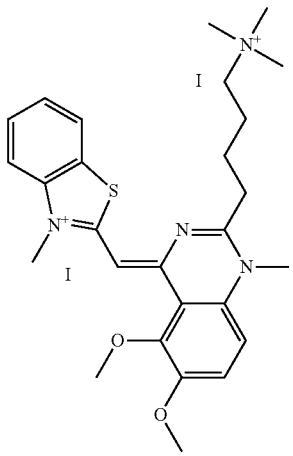

The DNA binding dye which can by far be used particularly well within the scope of the present invention is the LC480 Resolight Dye (Roche Diagnostics Catalogue No: 04 909 640 001). This dye can be used in high concentrations in the PCR and has the following chemical structure:

RO 27:

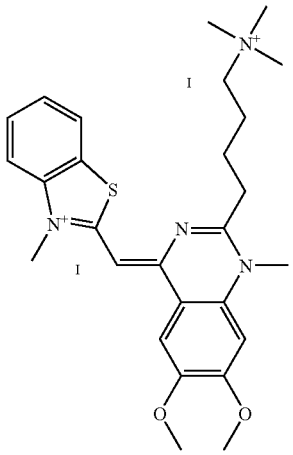

Details of the synthesis of this dye class are described in WO 2008/052742.

Alternatively all DNA binding dyes that are published and disclosed in WO 06/121423 can be used within the scope of the present method according to the invention. Two of these dyes such as for example LC Green and LC Green+ are commercially available (Idaho Technology, Cat. No: BCHM-ASY-0003 and BCHM-ASY-0006).

RO 27, LC Green and LC Green+ are fluorescent dyes from the group of HRM (high resolution melting) fluorescent dyes which can be used for so-called high resolution melting analyses after a real time PCR.

They have in common a low toxicity during the PCR amplification so that they can be used in higher concentrations without inhibiting the PCR.

Another class of dyes which is suitable for use in a method according to the invention are all dyes that are published and disclosed in U.S. Pat. No. 5,658,751. These are asymmetric cyanine dyes containing a benzothiazole or benzothiazolium group. Representatives of these types of dye are SYBR Green I, SYBR Green II, YO-PRO, TO-PRO, BEBO and BOXTO. Several of these dyes are commercially available, also including SYBR Green I, SYBR Green II, TO-PRO-1, YO-PRO-1, BEBO and BOXTO. SYBR Green I has the following chemical structure:

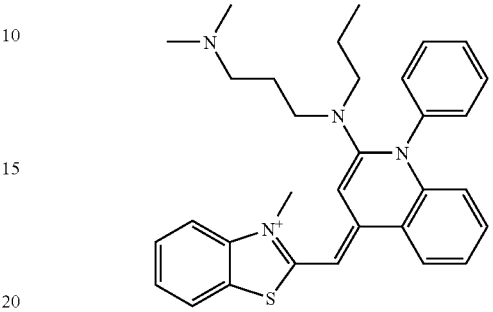

An example of a benzothiazole that can be used within the scope of the method according to the invention is BEBO:

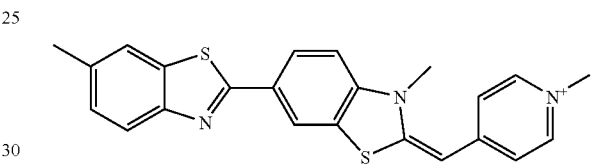

An additional class of dyes which is suitable for use in the method according to the invention are dyes which contain a benzoxazolium group. The following commercially available dyes are particularly suitable: SYTO-9 (Invitrogen Cat. No. S34854), SYTO-13 (Invitrogen Cat. No.: S7575), SYTO-16 (Invitrogen Cat. No.: S7578), SYTO-60 (Invitrogen Cat. No.: S11342), SYTO-62 (Invitrogen Cat. No.: S11344), SYTO-64 (Invitrogen Cat. No.: S34854) and SYTO-82 (Invitrogen Cat. No.: S11363).

In contrast the addition of ethidium bromide to dsDNA before the polyacrylamide gel electrophoresis does not allow the separated DNA to be directly detected. Ethidium bromide has the structural formula:

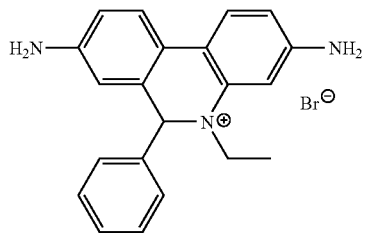

Thus, the method according to the invention excludes the use of ethidium bromide or similar intercalating dyes.

Before application to the gel an application buffer such as for example TBE or TAE is added to the PCR mixture containing the DNA binding dye according to the methods known from the prior art. In a suitable embodiment the gel matrix can consist of 0.02 to 6% w/v and preferably 0.5 to 4% agarose in a TBE buffer system. The electrophoretic separation at 10-150 V then preferably takes place in a horizontal direction for 10 to 180 minutes. In one embodiment the gel matrix can consist of a mixture of 4% to 25% w/v and preferably of 6-20% acrylamide/bisacrylamide in a TAE buffer system. A separation time of 10 to 30 minutes is preferred. The migration properties are determined in this case by the proportion of acrylamide as well as by the degree of cross-linking. This depends on the mixing ratio between acrylamide and bisacrylamide.

The electrophoretic separation is carried out at 20 to 250 V for 15 to 180 minutes. A separation time of 15 to 45 minutes is preferred. In a special embodiment the acrylamide matrix is in a capillary for carrying out a capillary gel electrophoresis (Schwartz, H. E., et al., J. Chromatogr. 559 (1991) 267-283; Guttman, A., Methods in Molecular Biology 52 (1996) 157-169: Capillary Gel Electrophoresis). It is a major advantage to be able to add these fluorescent dyes before the PCR reaction especially for the highly sensitive, highly resolving and rapid analysis of DNA fragments in the combination of PCR/capillary gel electrophoresis with LIF detection. Previously only the addition of these fluorescent dyes before the capillary gel electrophoresis was known (Garcia-Canas, V., J. Agric. Food Chem. 50 (2002)4497-4502; Sang, F., et al., J. Sep. Sci. 29 (2006)1275-1280).

After the electrophoretic separation of the nucleic acids by the classical gel electrophoresis, the nucleic acids are detected, for example, directly by means of a UV transilluminator or with the aid of imaging instruments such as the LumiImager (Roche Applied Science Cat. No. 2c 012 847).

During an examination of the dependencies of the direct detection of dsDNA on the size and the dependencies with regard to separation times (i.e., also the dependency on the voltage) it turned out that the detection can be dependent on the separation time in the case of small DNA fragments of 80-150 bp. Thus, in 6% polyacrylamide gels it is still possible to detect even small DNA fragments of 80-150 bp with the aid of RO 27 at 200 V voltage and 30 minutes separation time. It was also possible to directly detect 80 by PCR products without restaining in 20% gels with a separation time of 2 hours. In general it can be determined that shorter run times have a positive effect on the sensitivity of the nucleic acid detection within the scope of the method according to the invention.

Another aspect of the present invention concerns a kit containing:
  one or more reagents for carrying out a polymerase chain reaction
  a vessel containing a DNA binding dye with a benzothiazole, benzothiazolium or benzoxazolium group
  at least one gel matrix consisting of agarose or polyacrylamide.

The DNA binding dye is in turn preferably selected from a group consisting of RO 27, SYBR Green I, SYBR Green II, Syto 9, LC Green, LC Green+, SYTO-13, SYTO-16, SYTO-60, SYTO-62, SYTO-64 and SYTO-82 as described for the method according to the invention.

The gel matrix is shrink-wrapped in a foil to protect it against drying out. In addition the kit can contain an appropriate gel electrophoresis run buffer. It does not contain any staining dye.

The reagents for carrying out the polymerase chain reaction are usually a thermostable DNA polymerase such as for example Taq polymerase or a thermostable polymerase with additional reverse transcriptase activity, deoxynucleoside triphosphates, as well as suitable buffers and PCR additives such as for example magnesium chloride. The reagents can be present individually in the kit. One or more components including the DNA binding dye can also be present in the kit as a mixture in so-called master mixes. In addition such a kit can contain components for DNA sample preparation.

The invention is further elucidated by the following examples, publications and figures, the protective scope of which results from the patent claims. The described methods are to be understood as examples which still describe the subject matter of the invention even after modifications.

Example 1

Blockcycler PCR in the Presence of RO 27 and Subsequent Analysis of the PCR Product by Gel Electrophoresis Starting with genomic DNA isolated from CHO cells K1 ($5 \times 10^6$ cells/ml) a PCR reaction was carried out under standard conditions in which the GAPDH housekeeping gene was amplified as a target using primers known from the publication Eldering, J. A., et al., Biologicals 32 (2004)183-193. 3.2 µM RO 27 was added to the mixture before starting the PCR.

After the amplification 1:10 dilutions of the PCR mixture were prepared. 3 µl TBE sample buffer A named 5× was added to 12 µl of each dilution. 10 µl of each dilution was applied to a 6% polyacrylamide TBE gel. The electrophoresis was carried out for 30 minutes at 200 V. The subsequent detection was carried out after excitation for 2 seconds with a 520 nm light source in a LumiImager system.

Subsequently the gel was restained for 30 minutes with SYBR Green I according to the manufacturer's instructions (Invitrogen, Cat. No.: S7563).

FIG. 1 shows the visual result without (left side) and with restaining (right side). It can be seen that the presence of RO 27 alone in the PCR mixture is sufficient to detect the amplicon with adequate sensitivity. In contrast the restaining of the gel with SYBR Green I does not increase the sensitivity.

Example 2

Figure 2:
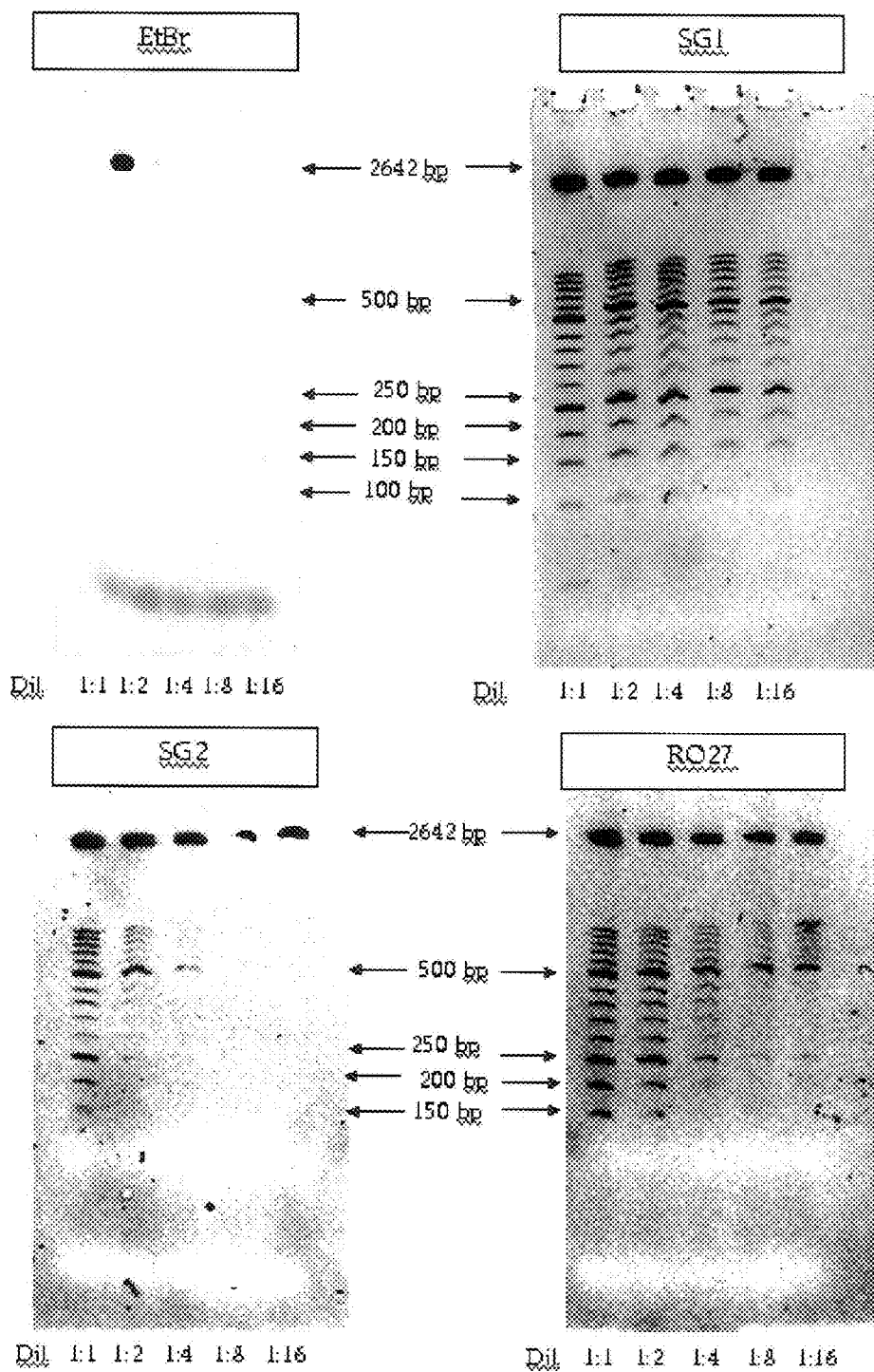
FIG. 2: Dilution series of a molecular weight marker in which 1.6 μm dye was added before the electrophoresis (EtBr=ethidium bromide, SG1=SYBR Green 1, SG2=SYBR Green 2, R27=RO 27).

Comparison of the Sensitivity of Various DNA Binding Dyes for the Detection of dsDNA in a Gel Electrophoresis In order to compare the detection limit of dsDNA with and without restaining using a molecular weight standard (length standard XIII, Roche Applied Science Cat. No.: 11 721 925 001) as an example and when using different DNA binding dyes as a function of the concentration of the molecular weight standard, various dilutions of the length standard were admixed in each case with 1.6 µM ethidium bromide, SYBR Green I, SYBR Green II or RO 27 before application to a gel system according to Example 1. The result is shown in FIG. 2. It can be seen that in particular SYBR Green I and RO 27 are suitable for a sensitive detection. No DNA is detectable when ethidium bromide is added to the length standard before application to the gel.

Example 3

Figure 3:
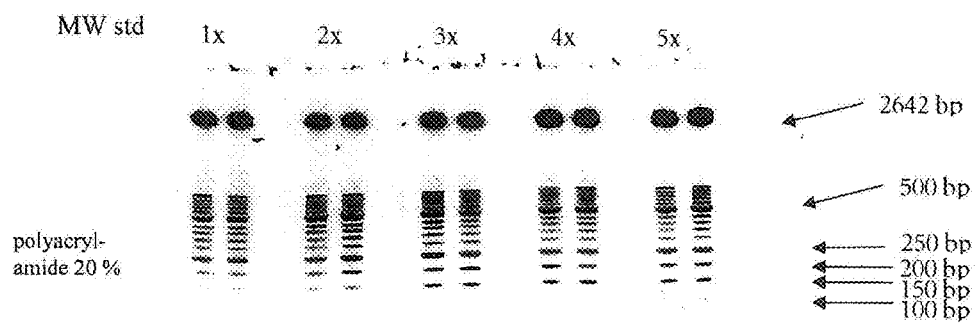
FIG. 3: Multiplication series of the molecular weight marker with constant concentrations of 3.2 μM RO 27 on a 20% polyacrylamide gel (left) and on a 6% polyacrylamide gel (right).
Figure 3:
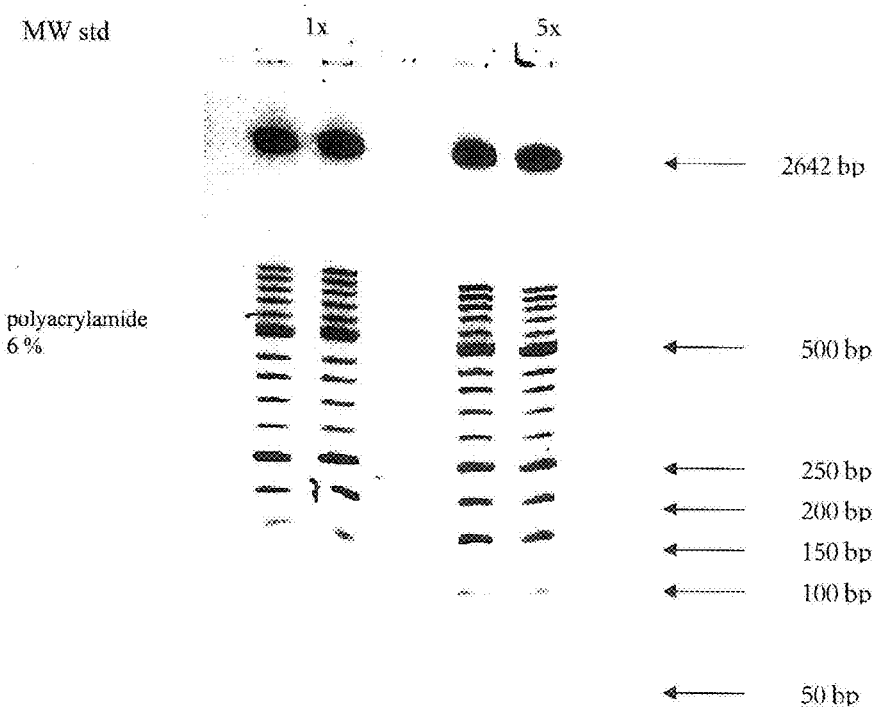
Figure 4A:
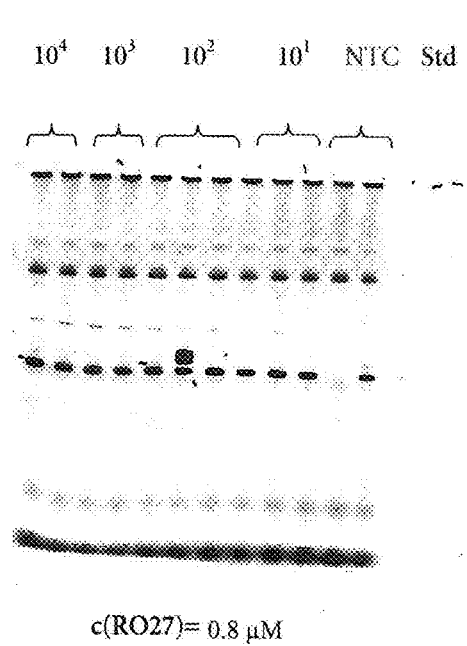
FIG. 4a: Polyacrylamide gel electrophoresis of PCR mixtures containing 0.8 μM RO 27 (left) or SYBR Green I (right) without restaining with SYBR Green II.
Figure 4A:
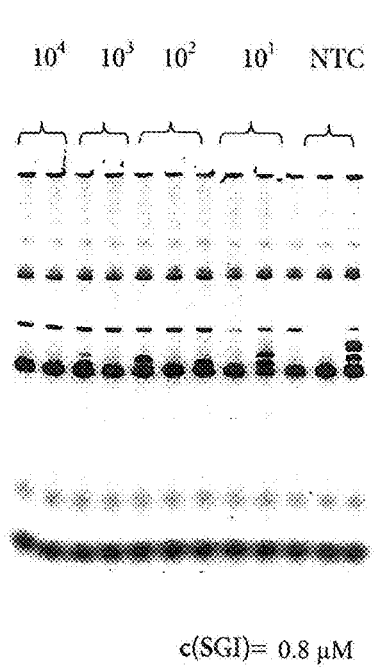
Figure 4B:
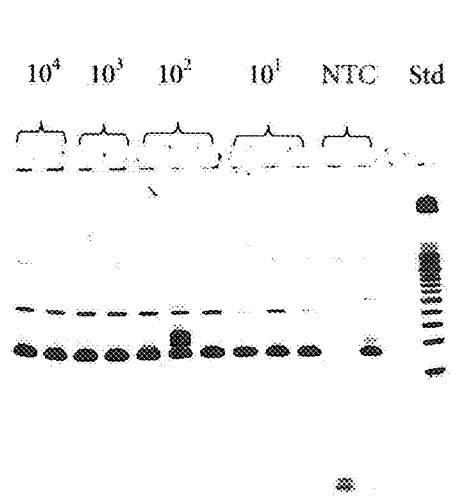
FIG. 4b: Polyacrylamide gel electrophoresis of PCR mixtures containing 0.8 μM RO 27 (left) or SYBR Green I (right) with restaining with SYBR Green II.
Figure 4B:
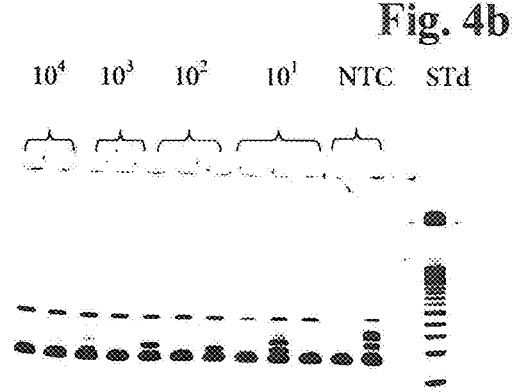
Figure 4C:
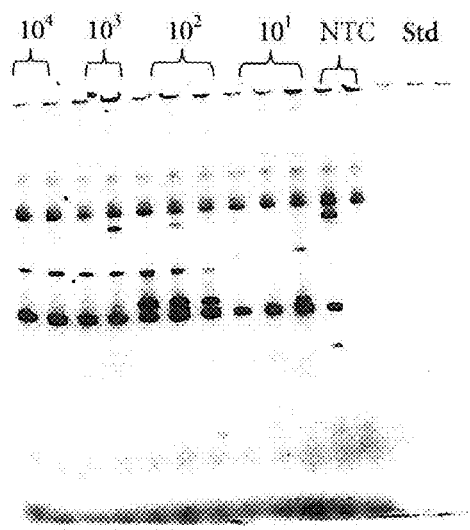
FIG. 4c: Polyacrylamide gel electrophoresis of PCR mixtures containing 4.0 μM RO 27 (left) or SYBR Green I (right) without restaining with SYBR Green II.
Figure 4C:
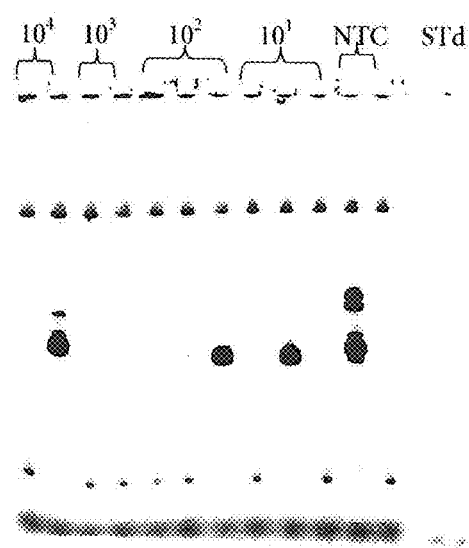
Figure 4D:
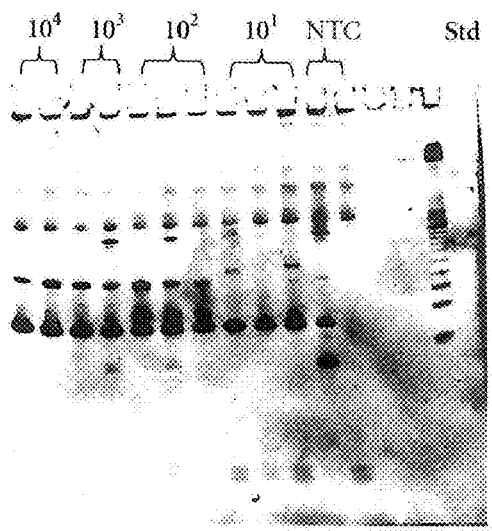
FIG. 4d: Polyacrylamide gel electrophoresis of PCR mixtures containing 4.0 μM RO 27 (left) or SYBR Green I (right) with restaining with SYBR Green II.
Figure 4D:
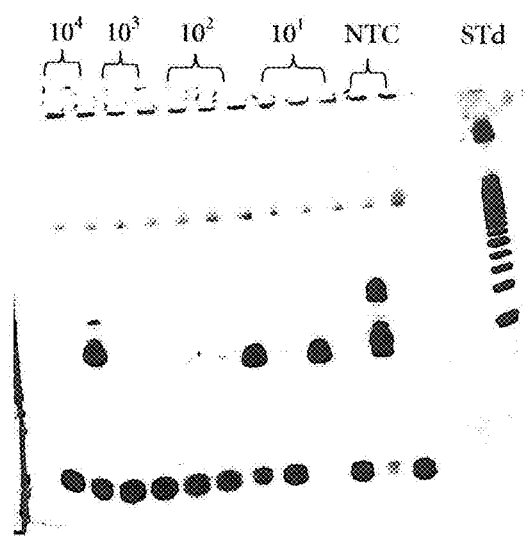

Assessment of the Sensitivity of RO 27 for Detecting DsDNA in Polyacrylamide Gels with Different Degrees of Cross-Linking Example 2 was repeated with samples containing in each case 3.2 µM RO 27 but different amounts of length standards (1-fold to 5-fold) on differently cross-linked gels (6% and 20%). FIG. 3 clearly shows that at the same molecular weight standard concentration (×5) and at the same RO 27 concentration (3.2 µM), the detectability of the 50-150 bp standards is only slightly better in the case of the 6% polyacrylamide gels. Thus, the method according to the invention can be used independently of the degree of cross-linking of the respective gel system.

Example 4

Real Time PCR Experiments with RO 27 Coupled with Gel Electrophoresis and the Detection of PCR Products without Staining with DNA Binding Dyes The aim of the experiments was to see whether real time PCR experiments with RO 27 as a universal detection dye with subsequent characterization of the PCR amplificates by gel electrophoresis can also be used for small PCR amplificates without any restaining. It is known from the prior art that DNA binding dyes containing a benzothiazolium or benzoxazolium group do not inhibit the PCR to any significant extent and can thus be used for real time PCR applications. Therefore, a PCR was carried out in which in each case 0.8 μM or 4 μM RO 27 or SYBR Green I was added to the PCR mixture before starting the amplification reaction.

The details of the amplification reactions were as follows:
Instrument: LIGHTCYCLER LC 2.0 with firmware version >4.02.0
LIGHTCYCLER: 20 μl capillaries
Dyes: 0.8 μM or 4 μM RO 27 or SYBR Green I
Template: Plasmid DNA containing 18s RNA gene sequence in different copy numbers ($10^4$, $10^3$, $10^2$, $10^1$)
Amplicon: 91 bp
LIGHTCYCLER programming:

| denaturation: | 95° C. | 10 min | 20° C./min | |
|---|---|---|---|---|
| amplification 1: | 95° C. | 10 sec | 20° C./min | } 10 × |
| | 60° C. | 15 sec | 20° C./min | single |
| | 72° C. | 20 sec | 20° C./min | |
| amplification 2: | 95° C. | 10 sec | 20° C./min | } 35 × |
| | 60° C. | 15 sec | 20° C./min | single |
| | 72° C. | 20 sec | 20° C./min | |
| melting curve: | 95° C. | 60 sec | 20° C./min | cont |
| | 40° C. | 60 sec | 20° C./min | |
| | 95° C. | 0 sec | 0.1° C./min | |
| cooling: | 40° C. | 30 sec | 20° C./min | |

Subsequently 10 μl of each of the mixtures was separated by gel electrophoresis similarly to Example 1.

The detection before and after additional restaining of the gel with SYBR Green I was also carried out according to Example 1.

The results are shown in FIG. 4 a-d. They show that even at a low RO 27 concentration (0.8 μM), the 80 bp bands are visible without restaining and all expected bands (except for primer dimer artifacts and the primers themselves) are detected. Restaining the gels with SYBR Green I does not result in a significant increase in the sensitivity of the detection. In this connection the advantage of RO 27 is that it can be used in even higher concentrations (4.0 μM) because the PCR reaction is not inhibited under these conditions in contrast to SYBR Green I. The detectability of weak DNA bands in the gel electrophoresis can thus be improved.

Example 5

Comparison of Various Gel Systems and Dyes

Similarly to Example 1 and 4 various dyes were added to a PCR reaction mixture before the amplification reaction. After the PCR was completed, the products were analyzed by gel electrophoresis without any further staining measures in a 6% polyacrylamide gel as well as in a 2% agarose gel. The result is shown in the following table.

| fluorescent dye | 6% polyacrylamide gel | 2% agarose gel | type of dye |
|---|---|---|---|
| RO 27 | + | + | benzothiazolium |
| SYBR Green I | + | + | benzothiazolium |
| SYBR Green II | + | not tested | benzothiazolium |
| Syto 9 | not tested | + | benzothiazolium |
| LC Green | not tested | + | , benzothiazolium |

What is claimed is:

1. A method for analyzing nucleic acids in a sample containing DNA comprising the steps of
adding a DNA binding dye to the sample to bind the nucleic acids in the sample and form a nucleic acid/DNA binding dye complex, wherein the DNA binding dye is RO 27 having a structure:

RO 27:

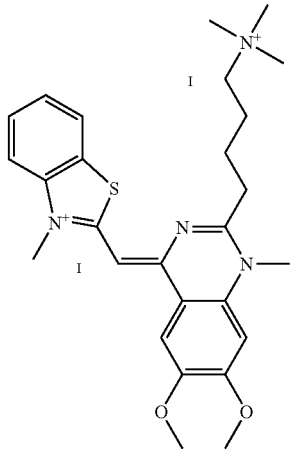

amplifying the nucleic acids by means of a polymerase chain reaction (PCR),
applying the amplified sample to a gel matrix,
separating the amplified nucleic acid molecules according to size by applying a voltage to the gel matrix,
exciting the molecules with light at a wavelength suitable for visualizing the dye complex, and
optically visualizating the nucleic acid/DNA binding dye complex, thereby analyzing the nucleic acids in the sample,
wherein the gel matrix is not pre-stained prior to separating the nucleic acid molecules and wherein the gel matrix is not stained after separating the nucleic acid molecules.

2. The method according to claim 1 wherein the amplification is measured in real time during the PCR with the aid of the DNA binding dye.

3. The method according to claim 1 wherein the gel matrix is polyacrylamide or agarose.

4. The method according to claim 3 wherein the gel matrix is polyacrylamide and is present in a capillary.

5. The method according to claim 1 wherein the DNA binding dye is added to the sample at a concentration of 1-10 μM.

6. The method according to claim 1 wherein the DNA binding dye is added to the sample at a concentration of 2-4 μM.

7. A kit for carrying out the method of claim 1 comprising reagents for carrying out a polymerase chain reaction,
a vessel containing RO 27, and
at least one polyacrylamide gel matrix.

* * * * *